United States Patent
Don Michael

(10) Patent No.: US 8,679,058 B2
(45) Date of Patent: Mar. 25, 2014

(54) SYSTEM FOR TREATING ARTERIAL OBSTRUCTIONS

(76) Inventor: T. Anthony Don Michael, Bakersfield, CA (US)

( * ) Notice: Subject to any disclaimer, the term of this patent is extended or adjusted under 35 U.S.C. 154(b) by 16 days.

(21) Appl. No.: 13/455,769

(22) Filed: Apr. 25, 2012

(65) Prior Publication Data

US 2012/0302953 A1 Nov. 29, 2012

Related U.S. Application Data

(60) Provisional application No. 61/478,693, filed on Apr. 25, 2011.

(51) Int. Cl.
*A61M 29/00* (2006.01)

(52) U.S. Cl.
USPC .................................................. 604/101.05

(58) Field of Classification Search
USPC ............ 604/101.01, 101.03, 101.05, 102.01, 604/102.03
See application file for complete search history.

(56) References Cited

U.S. PATENT DOCUMENTS

| | | | | |
|---|---|---|---|---|
| 4,581,017 A | * | 4/1986 | Sahota | 604/101.01 |
| 5,090,960 A | * | 2/1992 | Don Michael | 604/101.03 |
| 5,342,306 A | * | 8/1994 | Don Michael | 604/101.04 |
| 5,460,610 A | * | 10/1995 | Don Michael | 604/101.03 |
| 5,674,198 A | * | 10/1997 | Leone | 604/101.05 |
| 5,925,016 A | * | 7/1999 | Chornenky et al. | 604/96.01 |
| 6,485,502 B2 | * | 11/2002 | Don Michael et al. | 606/200 |
| 6,599,283 B1 | * | 7/2003 | Marzilli et al. | 604/509 |
| 6,666,880 B1 | * | 12/2003 | Chiu et al. | 623/1.11 |
| 7,169,171 B2 | * | 1/2007 | Don Michael | 623/1.11 |
| 7,524,303 B1 | * | 4/2009 | Don Michael et al. | 604/101.01 |
| 7,837,650 B1 | * | 11/2010 | Cox et al. | 604/110 |
| 2012/0259215 A1 | * | 10/2012 | Gerrans et al. | 600/435 |

* cited by examiner

*Primary Examiner* — Aarti B Berdichevsky
(74) *Attorney, Agent, or Firm* — Browdy and Neimark, PLLC

(57) ABSTRACT

An apparatus, a kit and a method for rapidly restoring blood flow through, and removing a clot from, a blood vessel by chemical dissolution. The essential components include an instrument for preventing the flow of debris downstream of the clot, a coronary catheter constructed to be introduced into the blood vessel and a double balloon catheter that has a tapered tip and that can form an enclosed space containing the clot and via which dissolution fluid can be brought into contact with the clot.

16 Claims, 3 Drawing Sheets

SYSTEM FOR TREATING ARTERIAL OBSTRUCTIONS

BACKGROUND OF THE INVENTION

The present invention relates to the treatment of arterial obstructions, and particularly blood clots in a blood vessel, such as a coronary artery.

It is known that most heart attacks are caused by the formation of a blood clot in a coronary artery and that the damage caused by a heart attack can be minimized by prompt medical intervention. In the case of a massive heart attack, 50% or more of the volume of the blockage consists of clot. Conventionally, this intervention primarily consists of a technique and apparatus that provides restoration of blood flow, with or without clot removal.

However, the appliances currently available for performing such an intervention are relatively costly, their utilization requires highly specialized training, and only a limited number of facilities are equipped to provide the necessary treatment. These facilities require a formal interventional cardiac catheterization laboratory.

Moreover, many heart attack victims, estimated at 50%, are too remote from a hospital equipped to carry out such a treatment to be able to receive the necessary treatment sufficiently quickly to minimize damage to heart muscle (minutes mean muscle death), and to prevent death.

SUMMARY OF THE INVENTION

With these difficulties in mind, the present invention provides a novel combination of devices, or instruments, that can be made more widely available and a method for their use that can be practiced with less specialized training.

More specifically, the invention provides a method and apparatus for rapidly reestablishing blood flow, in a blood vessel through which blood normally flows in a given direction and in which an obstructing clot has formed and then substantially eliminating the clot.

The apparatus includes:
a standard guide wire that may have any diameter suitable for insertion into the blood vessels that will be encountered in a treatment and which may, for example, have a diameter of 0.014" or 0.035", and may be hollow for use as part of a pressure sensor;
a first catheter, such as a coronary catheter, dimensioned to be inserted into the blood vessels and having an internal lumen dimensioned to allow passage of a first blocking device; and
a second catheter dimensioned to be inserted into the blood vessel in the direction of blood flow, the second catheter having:
 a longitudinal axis, a tapered distal end, a proximal end, and an outer lateral surface;
 a longitudinal lumen extending along the longitudinal axis from the proximal end and opening at the distal end;
 blood inlet openings extending from the lateral surface and communicating with the longitudinal lumen;
 blood outlet openings extending from the lateral surface at a location adjacent, but proximal to, the tapered distal end and communicating with said longitudinal lumen;
 a balloon inflation lumen extending from the proximal end and having two openings at the lateral surface at first and second locations spaced apart along the longitudinal axis and located between the blood inlet opening and the distal end, the balloon inflation lumen being isolated from the longitudinal lumen;
 a fluid delivery lumen extending from the proximal end to the lateral surface at a third location between the first and second location, and isolated from the longitudinal lumen and the balloon inflation lumen; and
 first and second balloons attached to the outer surface of the second catheter and each having an internal volume communicating with a respective one of the openings of the balloon inflation lumen at a respective one of the first and second locations.

According to an optional second embodiment of the invention, the apparatus further includes a blocking device comprising a tube and an expandable component for blocking a flow of debris from the clot at a location downstream of the clot with respect to the direction of blood flow.

The present invention also contemplates a kit composed of the components described above.

DETAILED DESCRIPTION OF THE INVENTION

Figure 1:
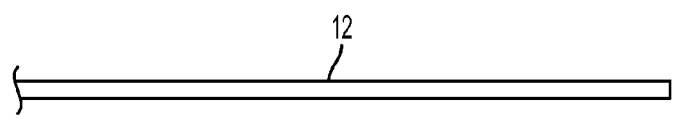
FIGS. 1 and 2 are elevational views of two devices, or instruments, employed in the practice of the present invention.

FIG. 1 shows a conventional guide wire 12 having, as is typical of guide wires, a diameter of the order of 0.014" or 0.035", and which may be hollow for use as part of a pressure sensor.

Figure 2:
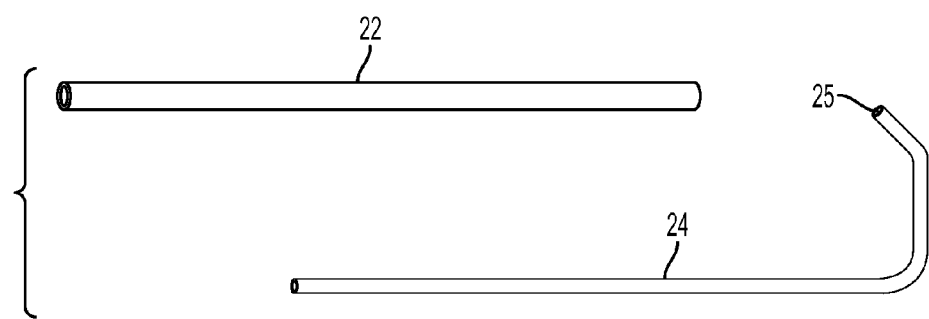

FIG. 2 shows two exemplary components of apparatus according to the present invention. The first component is an essentially straight, large diameter, guide catheter, or sheath, 22 having a diameter of the order of 8-10 Fr (Fr=French; 3 Fr=1 mm). The second component is a coronary catheter 24 having a pre-shaped distal end 25. Coronary catheter 24 may have an outer diameter of between 5 and 6 Fr and an inside of diameter between 1.2 and 1.8 mm, preferable, 1.4 or 1.6 mm, sufficient to allow passage of any of guide wire 12 or a sheath of sufficiently small diameter. Catheter 24 may, only by way of example, be a type of superselective coronary catheter. Both catheters 22 and 24 are resiliently flexible to the extent that they can be straightened out by guide wire 12, or a sheath, extending through them.

An example of catheter 22 is described in U.S. Pat. No. 4,581,017, which is incorporated herein by reference, and which discloses in detail the manner in which such a catheter is controlled to enter a coronary artery.

Other known types of coronary catheters can be employed in the practice of the present invention.

Figure 3:
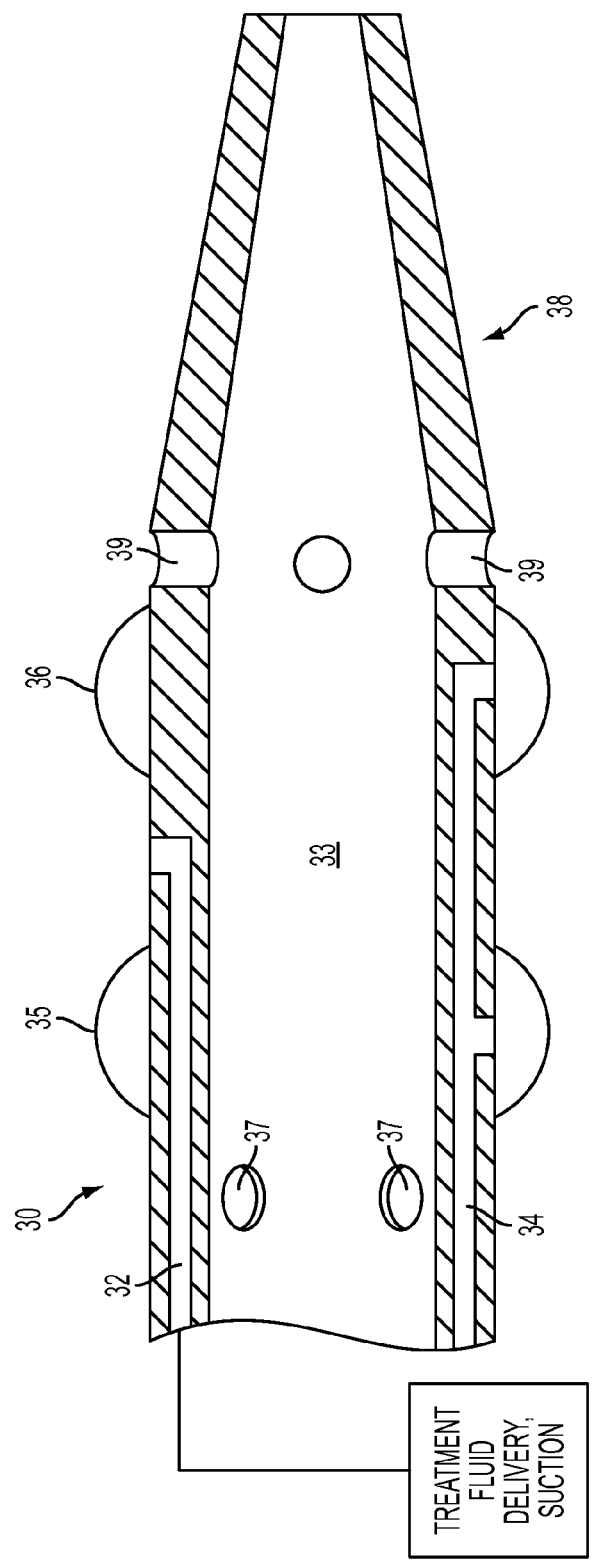
FIG. 3 is a cross-sectional view of a further instrument employed in the practice of the present invention.

FIG. 3 illustrates a double balloon catheter 30 having a treatment fluid/suction lumen 32, a longitudinal lumen 33, and a balloon inflation lumen 34, lumens 32 and 34 being formed in the catheter wall. Attached to the outer wall of catheter 30 are low pressure, high compliance blocking balloons 35 and 36, each having an internal volume communicating with outlet orifices of lumen 34, which extend to the outer wall of catheter 30. Balloons 35 and 36 thus differ in compliance, and thus the required expansion pressure, from the low compliance balloons employed to expand a stent after an angioplasty procedure, which employ catheters having an outer diameter of 4 Fr to 6 Fr.

Catheter 30 has, at its distal, or forward, end, a relatively long, progressively tapered tip 38 that may be fabricated in a manner to be more rigid than the body of the catheter in order to facilitate passage of the catheter through a clot.

Catheter 30 has a diameter of at least 4 Fr, and preferably 6 Fr, and tip 38 may have an axial length of 1 to 4 cm, the length presently preferred being 3 cm, although catheters having larger diameters and longer tips may be useful in certain situations and for certain patients. The free end of tip 38 may have an outer diameter of 0.018" and an inner diameter of 0.016" to accommodate a 0.014" guide wire. These dimensions may be increased if a larger diameter guide wire is to be used. However, in all cases, the inner diameter of the free end of tip 38 should be only slightly larger than the diameter of the guide wire. Tip 38 can be made of Teflon-nylon material.

Catheter 30 is also provided with blood bypass inlet openings 37 and blood bypass outlet openings 39 that communicate with longitudinal lumen 33 to form, with lumen 33, a blood bypass path intended to quickly establish blood flow around a clot when catheter 30 has been introduced into the blood vessel to extend across the clot, as will be described below. The open distal end of catheter 30, i.e., the tip, provides an additional blood bypass flow outlet opening. Bypass outlet openings 39 are preferably located in the wall of catheter 30 just ahead of tip 38, as shown.

Lumen 33 will have a diameter that is approximately 70-75% of the outer diameter of catheter 30. Preferably, the cross-sectional area of the blood bypass path, including the total area of openings 37 and the total area of openings 39, as well as lumen 33, will be 0.036". The wall thickness of catheter 30 may be of the order of 0.3 mm.

Equipment necessary for supplying treatment fluid and/or applying suction to lumen 32 is connected to the proximal end of catheter 30 outside of the patient's body.

Catheter 30 has a form similar to those disclosed in my U.S. Pats. Nos. 5,380,284 and 7,169,171, but differs essentially in that catheter 30 has a combination of two blocking balloons and a specially configured tip.

Figure 4:
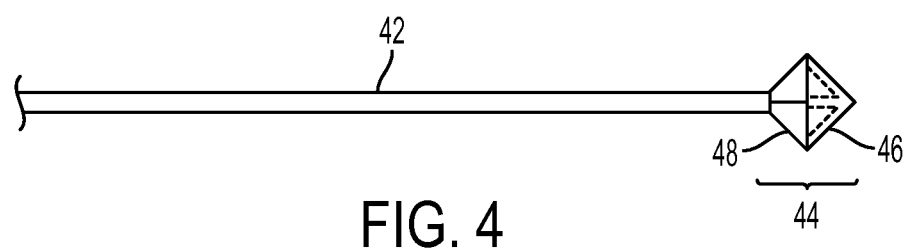
FIGS. 4 and 5 are elevational views of further instruments employed in the practice of the present invention.
Figure 5:
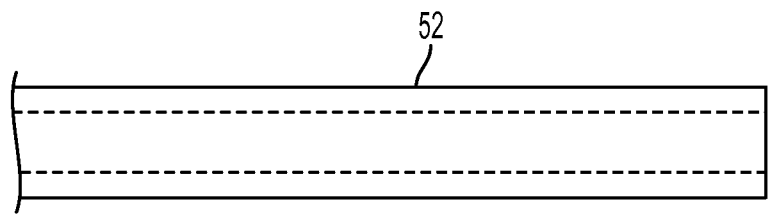

FIGS. 4 and 5 shows components of one example of the blocking device referred to earlier herein. The component shown in FIG. 4 is composed of a second guide wire 42 that carries, at its distal end, a collapsible, self expanding filter 44 constituted by a filter membrane 46 supported by a frame (not shown) and a plurality of struts 48 connecting membrane 46 to guide wire 42. Membrane 46 is fabricated to have a porosity sufficient to allow passage of blood components while retaining debris resulting from the dissolution or disintegration of a blood clot.

Filter 44 may be constructed as disclosed in issued U.S. Pat. No. 6,485,502, which issued on Nov. 26, 2002, the disclosure of which is incorporated herein by reference. Struts 48 and the frame supporting membrane 46 are made of resiliently deformable material that assures that the filter will expand when not confined and can be made of a material that is expandable and contractible However, filter 44 can be fabricated in any other suitable way that is known in the art.

FIG. 5 illustrates a sheath 52 having an internal diameter sufficient to allow passage of guide wire 42 and filter 44 in its collapsed state. By way of example, sheath 52 may have an outer diameter of 1.1 mm and an internal diameter, defining a lumen, of the order of 1 mm or less.

Basic Treatment Procedure

Phase 1: According to the basic procedure, after the affected artery has been identified, an incision is made in the groin, arm, or wrist, after which guide wire 12 is inserted through a needle into the artery exposed by the incision, through the artery exposed by the incision, and through the aorta, to a location close to, or in, the coronary artery containing the blockage to be removed.

Optionally, a conventional procedure is performed in which large diameter guide catheter, or sheath, 22 is first introduced through the artery exposed by the incision and into, and possibly through, the aorta in order to facilitate subsequent introduction of guide wire 12. Guide catheter or sheath 22 is used to guide the introduction of all catheters and filter used for this procedure, and for a modified procedure to be described below, and may be withdrawn at any time after guide wire 12 has been thus positioned.

Phase 2: Then, a second catheter, which may be any known type suitable for the purpose, such as coronary catheter 24, is introduced over guide wire 12 to the entrance to the affected coronary artery, and possibly into that artery.

Phase 3: Thereafter, the guide wire is withdrawn.

Phase 4: Then the exact location of the clot is determined, for example fluoroscopically and with the introduction of contrast fluid, through the second catheter.

Phase 5: After the clot has been thus located, the second catheter may be advanced to a point close to the clot.

Phase 6: Then, guide wire 12 is reintroduced, or another, steerable, guide wire is introduced, through and past the second catheter and through the clot.

Phase 7: The second catheter is then withdrawn and double balloon catheter 30 is introduced over the guide wire and advanced along the guide wire and then through and beyond the clot until the clot is straddled by the balloons. Tapered tip 38 of double balloon catheter 30 facilitates penetration of the catheter through the clot.

Phase 8: The guide wire is then withdrawn to open the blood bypass passage 37, 33, 39 in double balloon catheter 30 and thus immediately establish blood flow across the clot. Balloons 35 and 36 are then inflated to create an isolated region surrounding the clot. Then, a dissolution agent, or infusate, is introduced through lumen 32 to the region surrounding the outer surface of double balloon 30 catheter and enclosed by balloons 35 and 36 in order to dissolve the clot.

Phase 9: The dissolved clot material, debris and infusate are suctioned from the area being treated through lumen 32 and, after it has been determined that the clot has been at least substantially dissolved, a clot inhibiting substance, such as heparin or bivalarudin, is introduced into the treatment region. After an appropriate time has passed, the clot inhibiting substance will be withdrawn.

On rare occasions, parts of the clot may escape the confines of the balloons on the double balloon catheter. If this should occur, however, such parts will remain relatively close to the treatment region because the blood flow rate downstream of double balloon catheter 30 will be low as long as the balloons remain inflated. To determine whether a piece of clot has escaped, the region downstream of the double balloon catheter may be observed fluoroscopically with the aid of contrast fluid introduced through central lumen 33 of double balloon catheter 30. If a piece of clot is observed, further dissolution agent may be introduced via central lumen 33 and further fluoroscopic observations may then be undertaken until complete dissolution is confirmed.

Phase 10: Then, balloons 35 and 36 are deflated and double balloon catheter 30 is withdrawn from the patient. Thereafter, in accordance with standard procedure, the clot inhibiting substance can continue to be administered.

From time to time during the procedure, fluid with dissolved clot material can withdrawn via lumen 32, and a sample of the fluid withdrawn via lumen 32 may be analyzed in order to measure the concentration of dissolution fluid in the enclosed region. Contrast fluid may also be periodically introduced to monitor the progress of the dissolution treatment.

The various instruments employed in the procedure would be introduced through a manifold located outside of the patient's body. Such manifolds, and procedures for their use, are already well known in the art. For example, suitable manifolds for this purpose are marketed by the company Navilyst Medical, Inc. of Marlborough, Mass. One suitable manifold is marketed under the product name 3 port manifold.

Modified Procedure

A second clot removal treatment procedure according to the present invention would be performed in special situations, such as when a vein graft has been closed by a clot mass, or the clot mass is extensive and elongated, and the treatment can be performed in a suitable equipped facility such as a cath lab.

The modified procedure corresponds to the basic procedure, with the modifications to be described below.

Phases 1-5 are performed as described above.

Phase 6 is replaced by the following procedure. If necessary, catheter 24 may be withdrawn and sheath 52 is introduced through outer guide catheter 22. Filter 44 carried by guide wire 42 is initially stored in collapsed form within the longitudinal lumen of sheath 52. Sheath 52 with filter 44 retained therein, is advanced through, and to a point past, or downstream of, the clot. Then, sheath 52 is withdrawn from the patient's body to enable filter 44 to open automatically to block flow of debris in the artery at the location downstream of the clot.

Phase 7 is modified only in that only outer guide catheter 22 is withdrawn, catheter 24 having been withdrawn in the preceding phase.

Phase 8 is modified only to the extent that guide wire 42 is not withdrawn. Blood can continue to flow past the clot through inlet openings 37, lumen 33, outlet openings 39 and filter 44. Some blood can flow out of catheter 30 around guide wire 42 and through to central opening at the end of catheter 30.

Phase 10 is modified only to the extent that after catheter 30 is withdrawn, sheath 52 is reintroduced to capture, i.e collapse filter 44, which filter may then contain trapped debris, after which sheath 52, guide wire 42 and filter 44 are withdrawn from the patient.

It should be noted that one important function performed by the double balloon catheter disclosed herein is to provide blood flow across clot obstructing a blood vessel. This alone will restore the patient's condition. Thus, the application of the device and its construction recognizes the primary role of a shunt.

The apparatus and procedure according to the invention can be used to treat clots that occur in other locations, i.e., in other blocked arteries, including peripheral, renal, mesenteric and pulmonary arteries, in the brain, and in blocked veins, including peripheral and renal veins. With respect to arteries, this can include those of the leg, mainly the larger arteries such as the femoral and popliteal, and to arteries that supply the kidneys. Clots occurring in any of the three main arteries supplying the abdomen, would be eminently suitable candidates for this procedure. These arteries are the celiac, superior mesenteric and inferior mesenteric.

Clot obstructions in arteries may be caused by disease in the arteries but more commonly are due to embolism from the heart. The same considerations apply to the arteries in the arms, these being the subclavian and the brachial arteries.

With respect to veins, blood clots in veins are extremely common and arise due to abnormalities in clotting seen in cancer, after surgery of the hip, following immobilization, and during airplane flights. These blood clots can migrate into the pulmonary artery and cause death.

With respect to other vascular structures, patients having kidney dialysis frequently develop clotting in their arteriovenous shunts which are used to insert dialysis devices. This could be another condition treated according to the present invention.

The double balloon catheter described herein is mainly used when the inside wall of an artery ruptures, leading to a clot and what is described in the medical literature as an "acute coronary syndrome" colloquially referred to as STEMI. STEMI stands for ST change in the electrocardiogram in the situation of a myocardial infarction or a heart attack. Somewhat surprisingly, this is commoner in younger patients than in older populations. The present invention would be of value in treating clots in these young patients.

Furthermore, if a patient is seen with a stroke after three hours, the standard procedure is to deal with it with local delivery of blood thinners. There is a potential for using the present invention in this situation as well.

In younger patients, plaque, which constitutes the remainder of the obstruction, normally has an elastic consistency and allows larger catheters to traverse the obstructed area than one would mathematically calculate. In older patients, rupture of the plaque and clot seldom occurs as the plaques are hard, calcified and rigid. Thus, it is possible to use larger catheters in massive heart attacks, which are colloquially referred to as STEMI. Procedures using the apparatus according to the present invention can be employed on patients with STEMI myocardial infarctions in which clot predominates as a causative source of the problem.

The apparatus according to the invention can also be used, particularly according to the modified procedure described earlier herein, to dissolve a clot that blocks a stent, a frequent occurrence. In this situation it would be necessary to use the double balloon catheter and place it directly within the region enclosed by the stent, or with the balloons straddling the stent, to remove the clot that is contained within the stent. Whether or not a filter needs to be used will depend on the size of the artery in which the stent is implanted and the purpose of the catheter will change to one that primarily is focused on the removal of the clot. Since stents are put into all types of arteries ranging from the carotids and vertebrals to the head, the femorals in the legs, the renals in the kidneys, the mesenterics in the gut, the coronaries in the heart, the size of the arteries will vary from 10 mm to 3 mm.

The apparatus according to the invention can also be used to deliver materials mixed in with the blood, such as anticancer drugs or other agents such as stem cells and genes.

In certain situations, passage of the double balloon catheter in a vein may cause pieces to break off from the clot and flow downstream. If such a situation appears to be possible, the procedure employing the apparatus according to the invention for removing a clot from a vein may be carried out in the following alternative manner:

After the clot has been located, and possibly guide catheter 22 has been advanced to a point close to the clot, sheath 52 with filter 44 retracted therein is advanced through the clot and when the distal end of the sheath reaches an appropriate point beyond the clot, sheath 52 is withdrawn while guide wire 42 is held in place so that filter 44 is deployed to extend across the vein at a location downstream of the clot. Then, sheath 52 is completely removed and catheter 30 is advanced over guide wire 42 to a point at which balloons 35 and 36 straddle the clot. Then, the balloons are inflated, dissolution fluid is introduced to dissolve the clot, further treatments can be performed, and the apparatus removed, all as described earlier herein.

The following Table lists many of the uses of the apparatus according to the invention. The column labeled "THROUGH FLOW" identifies the importance of maintaining a bypass flow during treatment.

| | ORGAN | THROUGH FLOW | CLOT DISSOLUTION | COMMENTS |
|---|---|---|---|---|
| ARTERY | | | | |
| Coronary | Heart | Very important | Less important | Appropriate catheter selected depending on obstruction |
| Bypass Vein graft | Heart | Very Important | Very important | 1 or more clots may be present |
| Coronary veins | Heart | Not important | Very important | Entry through coronary sinus |
| Pulmonary veins | Lung | Not important | Very important | May be done medically or surgically |
| Carotid artery | Neck or brain | Very important | Important | Can be done in the neck or head |
| Renal Artery | Kidney | Important | Very important | The clots may arise from the heart |
| Femoral Artery | Legs | Less important | Very important | Includes the illiac, popliteal and superficial femoral |
| Mesenteric | Gastro-intestinal & Liver | Less important | Very important | There are 3 separate blood vessels supplying the Gastrointestinal tract |
| VEINS | | | | |
| Jugular veins | Brain (Cerebrum) | Not important | Very Important | This group applied to veins in the head supplying the brain |
| Deep veins of the calf | Calf | Unimportant | Very important | A major health problem which is unresolved |
| Large veins | Body | Not important | Very important | Local delivery-important |
| PROSTHETIC VALVES | Heart | Very important | Very important | Balloons sit astride the valve |
| STENTS | Heart Kidney Carotid Mesenteric Femoral | Important | Very Important | This is a significant problem with out a proper solution |

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Apparatus for eliminating a clot formed on an internal wall of a blood vessel through which blood flows in a given direction, said apparatus comprising:
   a guide wire; and
   a catheter dimensioned to be inserted over said guide wire into the blood vessel in the direction of blood flow, said catheter having:
      a longitudinal axis, a distal end, a proximal end, and an outer lateral surface, and said catheter has a main body portion and, at said distal end, a tapered tip;
      a longitudinal lumen extending along the longitudinal axis from said proximal end and opening at said distal end;
      at least one blood inlet opening extending from said lateral surface and communicating with said longitudinal lumen;
      at least one blood outlet opening extending from said lateral surface at a location adjacent said tapered distal end and communicating with said longitudinal lumen;
      a balloon inflation lumen extending from said proximal end to said lateral surface at first and second locations spaced apart along said longitudinal axis and located between said at least one blood inlet opening and said at least one blood outlet opening, and isolated from said longitudinal lumen;
      a treatment/fluid suction lumen extending from said proximal end to said lateral surface at a third location between said first and second locations, and isolated from said longitudinal lumen and said balloon inflation lumen; and
      first and second balloons attached to said outer surface of said catheter and each having an internal volume communicating with said balloon inflation lumen at a respective one of said first and second locations, wherein said tapered tip of said catheter is more rigid than said main body portion of said catheter and has an axial length of at least 1 cm.

2. The apparatus of claim 1, wherein said catheter has a diameter of 4-6 Fr, and said tapered tip has a free end with an inner diameter of the order of 0.016".

3. The apparatus of claim 1 wherein said tapered tip is made of a PTFE-nylon material.

4. The apparatus of claim 1, wherein said tapered tip has a free end with an inner diameter of the order of 0.002" greater than the diameter of said guide wire.

5. The apparatus of claim 1, wherein said tapered tip of said catheter has an axial length of 1 to 4 cm.

6. The apparatus of claim 5, wherein said tapered tip of said catheter has an axial length of 3 cm.

7. The apparatus of claim 1, further comprising a coronary catheter having a pre-shaped distal end and dimensioned to be inserted into the blood vessel over said guide wire and being configured to be directed to the vicinity of the clot.

8. The apparatus of claim 7, wherein said coronary catheter has a diameter of the order of 5-6 Fr.

9. A kit comprising:
the apparatus defined in claim 1;
a blocking device comprising a tube and an expandable component for blocking a flow of debris from the clot at a location downstream of the clot with respect to the direction of blood flow; and
a coronary catheter having a pre-shaped distal end and dimensioned to be inserted into the blood vessel over said guide wire and being configured to be directed to the vicinity of the clot.

10. The kit of claim 9, wherein said coronary catheter has a diameter of the order of 5-6 Fr.

11. The kit of claim 9, wherein said catheter has a diameter of 4-6 Fr, and said tapered tip has a free end with an inner diameter of the order of 0.016".

12. The kit of claim 9 wherein said tapered tip is made of a PTFE-nylon material.

13. The kit of claim 9 further comprising a straight guide sheath.

14. The kit of claim 9, wherein said coronary catheter has an internal lumen dimensioned to allow passage of said blocking device.

15. The kit of claim 9, wherein said tapered tip of said catheter has an axial length of 1 to 4 cm.

16. The kit of claim 15, wherein said tapered tip of said catheter has an axial length of 3 cm.

* * * * *